United States Patent
McKay

(10) Patent No.: US 8,188,038 B2
(45) Date of Patent: May 29, 2012

(54) OSTEOGENIC COMPOSITIONS CONTAINING A COLORING AGENT

(75) Inventor: William F. McKay, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 0 days.

(21) Appl. No.: 13/195,343

(22) Filed: Aug. 1, 2011

(65) Prior Publication Data

US 2011/0286939 A1    Nov. 24, 2011

Related U.S. Application Data

(62) Division of application No. 12/194,432, filed on Aug. 19, 2008, now Pat. No. 8,039,433.

(51) Int. Cl.
*A61K 38/16* (2006.01)
*A61K 38/17* (2006.01)
*A61K 38/18* (2006.01)

(52) U.S. Cl. .......... 514/7.6; 514/8.8; 514/16.7; 424/423

(58) Field of Classification Search .................. None
See application file for complete search history.

(56) References Cited

U.S. PATENT DOCUMENTS

| | | | |
|---|---|---|---|
| 4,950,483 A | 8/1990 | Ksander et al. | |
| 5,001,169 A | 3/1991 | Nathan et al. | |
| 5,681,873 A | 10/1997 | Norton et al. | |
| 6,030,967 A | 2/2000 | Marui et al. | |
| 7,172,629 B2 | 2/2007 | McKay | |
| 7,273,896 B2 | 9/2007 | Daniloff et al. | |
| 7,309,232 B2 | 12/2007 | Rutherford et al. | |
| 8,039,433 B2 * | 10/2011 | McKay | 514/7.6 |
| 2002/0018796 A1 | 2/2002 | Wironen | |
| 2002/0082694 A1 | 6/2002 | McKay | |
| 2004/0167637 A1 | 8/2004 | Biscup | |
| 2004/0192658 A1 | 9/2004 | Hunter et al. | |
| 2005/0065214 A1 | 3/2005 | Kronenthal | |
| 2005/0147643 A1 * | 7/2005 | Hunter et al. | 424/423 |
| 2006/0287676 A1 | 12/2006 | Prajapati et al. | |
| 2006/0292089 A1 | 12/2006 | Szymaitis | |
| 2007/0048382 A1 | 3/2007 | Meyer et al. | |
| 2007/0218424 A1 | 9/2007 | Vuorisalo et al. | |
| 2008/0109007 A1 | 5/2008 | Schwager et al. | |

OTHER PUBLICATIONS

International Search Report and Written Opinion for PCT/US2009/052360 mailed on Jan. 27, 2010.

* cited by examiner

*Primary Examiner* — Elizabeth C Kemmerer

(57) ABSTRACT

An osteogenic composition is provided for implantation at or near a target tissue site beneath the skin, the osteogenic composition comprising a growth factor and a coloring agent, wherein the coloring agent imparts color to the growth factor to allow the user to see the growth factor at or near the target tissue site. In some embodiments, a method is provided for accelerating bone repair, the method comprising mixing bone morphogenic protein-2 and a coloring agent to form a mixture; applying the mixture to a surface of a porous collagen matrix, wherein the coloring agent allows the user to see bone morphogenic protein-2 distribution on or in the porous collagen matrix; and implanting the porous collagen matrix at or near a target tissue site in need of bone repair.

9 Claims, No Drawings

OSTEOGENIC COMPOSITIONS CONTAINING A COLORING AGENT

CROSS REFERENCE TO RELATED APPLICATION

This application is a divisional of U.S. patent application Ser. No. 12/194,432, filed Aug. 19, 2008 and now issued as U.S. Pat. No. 8,039,433.

BACKGROUND

Bone is a composite material that is composed of impure hydroxyapatite, collagen and a variety of non-collagenous proteins, as well as embedded and adherent cells. Due to disease, a congenital defect or an accident, a person may lose or be missing part or all of one or more bones or regions of cartilage in his or her body, and/or have improper growth or formation of bone and/or cartilage.

Mammalian bone tissue is known to contain one or more proteinaceous materials that are active during growth and natural bone healing. These materials can induce a developmental cascade of cellular events that results in bone formation. Typically, the developmental cascade of bone formation involves chemotaxis of mesenchymal cells, proliferation of progenitor cells, differentiation of cartilage, vascular invasion, bone formation, remodeling and marrow differentiation.

When bone is damaged, often bone grafting procedures are performed to repair the damaged bone especially in cases where the damage is complex, poses a significant risk to the patient, and/or fails to heal properly. Bone grafting is also used to help fusion between vertebrae, correct deformities, or provide structural support for fractures of the spine. In addition to fracture repair, bone grafting is also used to repair defects in bone caused by birth defects, traumatic injury, or surgery for bone cancer.

There are at least three ways in which a bone graft can help repair a defect. The first is called osteogenesis, the formation of new bone within the graft. The second is osteoinduction, a process in which molecules contained within the graft (e.g., bone morphogenic proteins) convert the patient's cells into cells that are capable of forming bone. The third is osteoconduction, a physical effect by which a matrix often containing graft material acts as a scaffold on which bone and cells in the recipient are able to form new bone.

The source of bone for grafting can be obtained from bones in the patient's own body (e.g., hip, skull, ribs, etc.), called autograft, or from bone taken from other people that is frozen and stored in tissue banks, called allograft. The source of bone may also be derived from animals of a different species called a xenograft.

Some grafting procedures utilize a variety of natural and synthetic matrixes with or instead of bone (e.g., collagen, silicone, acrylics, hydroxyapatite, calcium sulfate, ceramics, etc.). To place the matrix at the bone defect, the surgeon makes an incision in the skin over the bone defect and shapes the matrix to fit into the defect. As persons of ordinary skill are aware, growth factors (e.g., bone morphogenic protein-2) may be placed on the matrix in order to spur the patient's body to begin the formation of new bone and/or cartilage. These growth factors act much like a catalyst, encouraging the necessary cells (including, but not limited to, mesenchymal stem cells, osteoblasts, and osteoclasts) to more rapidly migrate into the matrix, which is eventually resorbed via a cell-mediated process and newly formed bone is deposited at or near the bone defect. In this manner severe fractures may be healed, and vertebrae successfully fused.

Sometimes when the surgeon manipulates the matrix to place it in the bone defect, excessive amounts of growth factor (e.g., bone morphogenic protein) may leak from the matrix, which may reduce a stable microenvironment for new bone and/or cartilage growth. It also may cause the matrix to fail to retain its full efficacy over time to maximally promote bone and/or cartilage growth at a target site. Thus, there is a need to develop new osteogenic compositions and methods that improve bone and/or cartilage repair.

SUMMARY

Compositions and methods are provided that improve bone and/or cartilage repair. Through the use of these osteogenic compositions, the growth of bone, cartilage and/or related tissue may be facilitated. In some embodiments, the osteogenic composition allows the user (e.g., surgeon, nurse, assistant, etc.) to see a visibly discernible color (e.g., green, blue, etc.) so that the user can see the application of the growth factor. In some embodiments, the osteogenic composition is applied to a matrix that is a contrasting color to the composition (e.g., green or blue composition on white or beige matrix) so that the user can see the consistency of the application of the growth factor on the matrix or see unwanted leakage of the growth factor from the matrix. In this way, the matrix can maintain its efficacy over time to promote bone growth at a target site.

In some embodiments, an osteogenic composition is provided for implantation at or near a target tissue site beneath the skin, the osteogenic composition comprising a growth factor and a coloring agent, wherein the coloring agent imparts color to the growth factor to allow the user to implant the growth factor at or near the target tissue site.

In some embodiments, an osteogenic composition is provided for implantation at or near a target tissue site beneath the skin, the osteogenic composition comprising: a growth factor; a coloring agent; and a biodegradable matrix comprising a porous collagen surface, wherein upon mixing the coloring agent with the growth factor, the coloring agent imparts color to the growth factor to allow the user to see the growth factor distribution on or in the porous collagen surface.

In some embodiments, a method is provided for accelerating bone repair in a patient in need of such treatment, the method comprising mixing bone morphogenic protein-2 and a coloring agent to form a mixture, wherein the coloring agent imparts color to the mixture; applying the mixture to a surface of a porous collagen matrix, wherein the coloring agent allows the user to see bone morphogenic protein-2 distribution on or in the porous collagen matrix; and implanting the porous collagen matrix at or near a target tissue site in need of bone repair Additional features and advantages of various embodiments will be set forth in part in the description that follows, and in part will be apparent from the description, or may be learned by practice of various embodiments. The objectives and other advantages of various embodiments will be realized and attained by means of the elements and combinations particularly pointed out in the description and appended claims.

DETAILED DESCRIPTION

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present application. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values are as precise as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, e.g., 5.5 to 10.

Additionally, unless defined otherwise or apparent from context, all technical and scientific terms used herein have the same meanings as commonly understood by one of ordinary skill in the art to which this invention belongs.

Unless explicitly stated or apparent from context, the following terms or phrases have the definitions provided below:

DEFINITIONS

It is noted that, as used in this specification and the appended claims, the singular forms "a," "an," and "the," include plural referents unless expressly and unequivocally limited to one referent. Thus, for example, reference to "a matrix" includes one, two, three or more matrices.

The term "biodegradable" includes that all or parts of the matrix will degrade over time by the action of enzymes, by hydrolytic action and/or by other similar mechanisms in the human body. In various embodiments, "biodegradable" includes that a matrix (e.g., microparticle, microsphere, etc.) can break down or degrade within the body to non-toxic components after or while a therapeutic agent has been or is being released. By "bioerodible" it is meant that the matrix will erode or degrade over time due, at least in part, to contact with substances found in the surrounding tissue, fluids or by cellular action. By "bioabsorbable" or "bioresorbable" it is meant that the osteogenic composition will be broken down and absorbed within the human body, for example, by a cell or tissue. "Biocompatible" means that the matrix will not cause substantial tissue irritation or necrosis at the target tissue site.

The term "mammal" refers to organisms from the taxonomy class "mammalian," including but not limited to humans, other primates such as chimpanzees, apes, orangutans and monkeys, rats, mice, cats, dogs, cows, horses, etc.

The term "target tissue site" is intended to mean the location of the tissue to be treated. Typically the placement site of the matrix will be the same as the target site to provide for optimal targeted drug delivery. However, the present application also contemplates positioning the matrix at a placement site at or near the target site such that the therapeutic agent can be delivered to the surrounding vasculature, which carries the agent to the desired nearby target site. As used herein, the term "at or near" includes embodiments where the placement site and target site are within close proximity.

A "therapeutically effective amount" or "effective amount" is such that when administered, the drug results in alteration of the biological activity, such as, for example, promotion of bone, cartilage and/or other tissue (e.g., vascular tissue) growth, inhibition of inflammation, reduction or alleviation of pain, improvement in the condition through inhibition of an immunologic response, etc. The dosage administered to a patient can be as single or multiple doses depending upon a variety of factors, including the drug's administered pharmacokinetic properties, the route of administration, patient conditions and characteristics (sex, age, body weight, health, size, etc.), extent of symptoms, concurrent treatments, frequency of treatment and the effect desired. In some embodiments the formulation is designed for immediate release. In other embodiments the formulation is designed for sustained release. In other embodiments, the formulation comprises one or more immediate release surfaces and one or more sustained release surfaces. In some embodiments, the osteogenic composition comprises an effective amount of a growth factor.

The phrase "immediate release" is used herein to refer to one or more therapeutic agent(s) that is introduced into the body and that is allowed to dissolve in or become absorbed at the location to which it is administered, with no intention of delaying or prolonging the dissolution or absorption of the drug.

The phrases "sustained release" and "sustain release" (also referred to as extended release or controlled release) are used herein to refer to one or more therapeutic agent(s) that is introduced into the body of a human or other mammal and continuously or continually releases a stream of one or more therapeutic agents over a predetermined time period and at a therapeutic level sufficient to achieve a desired therapeutic effect throughout the predetermined time period. Reference to a continuous or continual release stream is intended to encompass release that occurs as the result of biodegradation in vivo of the drug bead, foam and/or component thereof, or as the result of metabolic transformation or dissolution of the therapeutic agent(s) or conjugates of therapeutic agent(s).

The "matrix" of the present application is utilized as a scaffold for bone and/or cartilage repair, regeneration, and/or augmentation. Typically, the matrix provides a 3-D matrix of interconnecting pores, which acts as a pliant scaffold for cell migration. The morphology of the matrix guides cell migration and cells are able to migrate into or over the matrix, respectively. The cells then are able to proliferate and synthesize new tissue and form bone and/or cartilage.

The terms "treating" and "treatment" when used in connection with a disease or condition refer to executing a protocol that may include osteochondral repair procedure, administering one or more drugs to a patient (human or other mammal), in an effort to alleviate signs or symptoms of the disease or condition or immunological response. Alleviation can occur prior to signs or symptoms of the disease or condition appearing, as well as after their appearance. Thus, treating or treatment includes preventing or prevention of disease or undesirable condition. In addition, treating, treatment, preventing or prevention do not require complete alleviation of signs or symptoms, does not require a cure, and specifically includes protocols that have only a marginal effect on the patient. In some embodiments, the osteogenic composition can be used to treat subchondral, osteochondral, hyaline cartilage and/or condyle defects.

The term "subchondral" includes an area underlying joint cartilage. The term "subchondral bone" includes a very dense, but thin layer of bone just below a zone of cartilage and above the cancellous or trabecular bone that forms the bulk of the bone structure of the limb. "Osteochondral" includes a combined area of cartilage and bone where a lesion or lesions can occur. "Osteochondral defect" includes a lesion which is a composite lesion of cartilage and subchondral bone. "Hyaline cartilage" includes cartilage containing groups of isogenous chondrocytes located within lacunae cavities which are scattered throughout an extracellular collagen matrix. A "condyle" includes a rounded articular surface of the extremity of a bone.

The phrase "osteogenic composition" refers to a composition that comprises a substance that promotes bone growth. In some embodiments, osteogenic compositions as described herein can be delivered to other surgical sites, particularly sites at which bone growth is desired. These include, for instance, the repair of spine (e.g., vertebrae fusion) cranial defects, iliac crest back-filling, acetabular defects, in the repair of tibial plateau, long bone defects, spinal site defects or the like. Such methods can be used to treat major or minor defects in these or other bones caused by trauma (including open and closed fractures), disease, or congenital defects, for example.

The term "carrier" includes a diluent, adjuvant, buffer, excipient, or vehicle with which a composition can be administered. Carriers can include sterile liquids, such as, for example, water and oils, including oils of petroleum, animal, vegetable or synthetic origin, such as, for example, peanut oil, soybean oil, mineral oil, sesame oil, or the like. The growth factor may include a carrier.

The term "excipient" includes a non-therapeutic agent added to a pharmaceutical composition to provide a desired consistency or stabilizing effect. Excipients for parenteral formulations, include, for example, oils (e.g., canola, cottonseed, peanut, safflower, sesame, soybean), fatty acids and salts and esters thereof (e.g., oleic acid, stearic acid, palmitic acid), alcohols (e.g., ethanol, benzyl alcohol), polyalcohols (e.g., glycerol, propylene glycols and polyethylene glycols, e.g., PEG 3350), polysorbates (e.g., polysorbate 20, polysorbate 80), gelatin, albumin (e.g., human serum albumin), salts (e.g., sodium chloride), succinic acid and salts thereof (e.g., sodium succinate), amino acids and salts thereof (e.g., alanine, histidine, glycine, arginine, lysine), acetic acid or a salt or ester thereof (e.g., sodium acetate, ammonium acetate), citric acid and salts thereof (e.g., sodium citrate), benzoic acid and salts thereof, phosphoric acid and salts thereof (e.g., monobasic sodium phosphate, dibasic sodium phosphate), lactic acid and salts thereof, polylactic acid, glutamic acid and salts thereof (e.g., sodium glutamate), calcium and salts thereof (e.g., $CaCl_2$, calcium acetate), phenol, sugars (e.g., glucose, sucrose, lactose, maltose, trehalose), erythritol, arabitol, isomalt, lactitol, maltitol, mannitol, sorbitol, xylitol, nonionic surfactants (e.g., TWEEN 20, TWEEN 80), ionic surfactants (e.g., sodium dodecyl sulfate), chlorobutanol, DMSO, sodium hydroxide, glycerin, m-cresol, imidazole, protamine, zinc and salts thereof (e.g, zinc sulfate), thimerosal, methylparaben, propylparaben, carboxymethylcellulose, chlorobutanol, and heparin, The growth factor may include an excipient.

The term "lyophilized" or "freeze-dried" includes a state of a substance that has been subjected to a drying procedure such as lyophilization, where at least 50% of moisture has been removed. The growth factor may be lyophilized or freeze-dried.

A "preservative" includes a bacteriostatic, bacteriocidal, fungistatic or fungicidal compound that is generally added to formulations to retard or eliminate growth of bacteria or other contaminating microorganisms in the formulations. Preservatives include, for example, benzyl alcohol, phenol, benzalkonium chloride, m-cresol, thimerosol, chlorobutanol, methylparaben, propylparaben and the like. Other examples of pharmaceutically acceptable preservatives can be found in the USP. The growth factor may have preservatives or be preservative free.

Reference will now be made in detail to certain embodiments of the invention. While the invention will be described in conjunction with the illustrated embodiments, it will be understood that they are not intended to limit the invention to those embodiments. On the contrary, the invention is intended to cover all alternatives, modifications, and equivalents that may be included within the invention as defined by the appended claims.

Compositions and methods are provided that improve bone and/or cartilage repair. Through the use of these osteogenic compositions, the growth of bone, cartilage and/or related tissue may be facilitated. In some embodiments, the osteogenic composition allows the user (e.g., surgeon, nurse, assistant, etc.) to see a visibly discernible color (e.g., green, blue, etc.) so that the user can see the application of the growth factor. In some embodiments, the osteogenic composition is applied to a matrix that is a contrasting color to the composition (e.g., green or blue composition on white or beige matrix) so that the user can see the consistency of the application of the growth factor on the matrix or see unwanted leakage of the growth factor from the matrix. In this way, the matrix can maintain its efficacy over time to promote bone growth at a target site.

The headings below are not meant to limit the disclosure in any way; embodiments under any one heading may be used in conjunction with embodiments under any other heading.

Matrix

The matrix provides a tissue scaffold for the cells to guide the process of tissue formation in vivo in three dimensions. The morphology of the matrix guides cell migration and cells are able to migrate into or over the scaffold. The cells then are able to proliferate and synthesize new tissue and form bone and/or cartilage. In some embodiments, one or more tissue matrices are stacked on one another.

In some embodiments, the matrix comprises a plurality of pores. In some embodiments, at least 10% of the pores are between about 10 micrometers and about 500 micrometers at their widest points. In some embodiments, at least 20% of the pores are between about 50 micrometers and about 150 micrometers at their widest points. In some embodiments, at least 30% of the pores are between about 30 micrometers and about 70 micrometers at their widest points. In some embodiments, at least 50% of the pores are between about 10 micrometers and about 500 micrometers at their widest points. In some embodiments, at least 90% of the pores are between about 50 micrometers and about 150 micrometers at their widest points. In some embodiments, at least 95% of the pores are between about 100 micrometers and about 250 micrometers at their widest points. In some embodiments, 100% of the pores are between about 10 micrometers and about 300 micrometers at their widest points.

In some embodiments, the matrix has a porosity of at least about 30%, at least about 50%, at least about 60%, at least about 70%, at least about 90%. The pore may support ingrowth of cells, formation or remodeling of bone, cartilage and/or vascular tissue.

The matrix may comprise natural and/or synthetic material. For example, the tissue scaffold may comprise poly (alpha-hydroxy acids), poly (lactide-co-glycolide) (PLGA), polylactide (PLA), polyglycolide (PG), polyethylene glycol (PEG) conjugates of poly (alpha-hydroxy acids), polyorthoesters (POE), polyaspirins, polyphosphagenes, collagen, hydrolyzed collagen, gelatin, hydrolyzed gelatin, fractions of hydrolyzed gelatin, elastin, starch, pre-gelatinized starch, hyaluronic acid, chitosan, alginate, albumin, fibrin, vitamin E analogs, such as alpha tocopheryl acetate, d-alpha tocopheryl succinate, D,L-lactide, or L-lactide, -caprolactone, dextrans, vinylpyrrolidone, polyvinyl alcohol (PVA), PVA-g-PLGA, PEGT-PBT copolymer (polyactive), methacrylates, poly(N-isopropylacrylamide), PEO-PPO-PEO (pluronics), PEO-PPO-PAA copolymers, PLGA-PEO-PLGA, PEG-PLG, PLA-PLGA, poloxamer 407, PEG-PLGA-PEG triblock copolymers, SAIB (sucrose acetate isobutyrate), polydioxanone, methylmethacrylate (MMA), MMA and N-vinylpyyrolidone, polyamide, oxycellulose, copolymer of glycolic acid and trimethylene carbonate, polyesteramides, polyetheretherketone, polymethylmethacrylate, silicone, hyaluronic acid, chitosan, or combinations thereof.

In some embodiments, the matrix may comprise a resorbable ceramic (e.g., hydroxyapatite, tricalcium phosphate, bioglasses, calcium sulfate, etc.) tyrosine-derived polycarbonate poly (DTE-co-DT carbonate), in which the pendant group via the tyrosine—an amino acid—is either an ethyl ester (DTE) or free carboxylate (DT) or combinations thereof.

In some embodiments, the matrix comprises collagen. Exemplary collagens include human or non-human (bovine, ovine, and/or porcine), as well as recombinant collagen or combinations thereof. Examples of suitable collagen include, but are not limited to, human collagen type I, human collagen type II, human collagen type III, human collagen type IV, human collagen type V, human collagen type VI, human collagen type VII, human collagen type VIII, human collagen type IX, human collagen type X, human collagen type XI, human collagen type XII, human collagen type XIII, human collagen type XIV, human collagen type XV, human collagen type XVI, human collagen type XVII, human collagen type XVIII, human collagen type XIX, human collagen type XXI, human collagen type XXII, human collagen type XXIII, human collagen type XXIV, human collagen type XXV, human collagen type XXVI, human collagen type XXVII, and human collagen type XXVIII, or combinations thereof. Collagen further may comprise hetero- and homo-trimers of any of the above-recited collagen types. In some embodiments, the collagen comprises hetero- or homo-trimers of human collagen type I, human collagen type II, human collagen type III, or combinations thereof.

In some embodiments, the matrix comprises collagen-containing biomaterials from the implant market which, when placed in a bone defect, provide scaffolding around which the patient's new bone will grow, gradually replacing the carrier matrix as the target site heals. Examples of suitable carrier matrices may include, but are not limited to, the MasterGraft® Matrix produced by Medtronic Sofamor Danek, Inc., Memphis, Tenn.; MasterGraft® Putty produced by Medtronic Sofamor Danek, Inc., Memphis, Tenn.; Absorbable Collagen Sponge ("ACS") produced by Integra LifeSciences Corporation, Plainsboro, N.J.; bovine skin collagen fibers coated with hydroxyapatite, e.g. Healos®. marketed by Johnson & Johnson, USA; collagen sponges, e.g. Hemostagene® marketed by Coletica S A, France, or e.g. Helisat® marketed by Integra Life Sciences Inc., USA; and Collagraft® Bone Graft Matrix produced by Zimmer Holdings, Inc., Warsaw, Ind.

In some embodiments, the embodiments the matrix may comprise particles of bone-derived materials. The bone-derived material may include one or more of non-demineralized bone particles, demineralized bone particles, lightly demineralized bone particles, and/or deorganified bone particles.

In some embodiments, the matrix may be seeded with harvested bone cells and/or bone tissue, such as for example, cortical bone, autogenous bone, allogenic bones and/or xenogenic bone. In some embodiments, the matrix may be seeded with harvested cartilage cells and/or cartilage tissue (e.g., autogenous, allogenic, and/or xenogenic cartilage tissue). For example, before insertion into the target tissue site, the matrix can be wetted with the graft bone tissue/cells, usually with bone tissue/cells aspirated from the patient, at a ratio of about 3:1, 2:1, 1:1, 1:3 or 1:2 by volume. The bone tissue/cells are permitted to soak into the matrix provided, and the matrix may be kneaded by hand or machine, thereby obtaining a pliable consistency that may subsequently be packed into the bone defect. In some embodiments, the matrix provides a malleable, non-water soluble carrier that permits accurate placement and retention at the implantation site.

The matrix may contain an inorganic material, such as an inorganic ceramic and/or bone substitute material. Exemplary inorganic materials or bone substitute materials include but are not limited to aragonite, dahlite, calcite, amorphous calcium carbonate, vaterite, weddellite, whewellite, struvite, urate, ferrihydrate, francolite, monohydrocalcite, magnetite, goethite, dentin, calcium carbonate, calcium sulfate, calcium phosphosilicate, sodium phosphate, calcium aluminate, calcium phosphate, hydroxyapatite, alpha-tricalcium phosphate, dicalcium phosphate, β-tricalcium phosphate, tetracalcium phosphate, amorphous calcium phosphate, octacalcium phosphate, BIOGLASS™, fluoroapatite, chlorapatite, magnesium-substituted tricalcium phosphate, carbonate hydroxyapatite, substituted forms of hydroxyapatite (e.g., hydroxyapatite derived from bone may be substituted with other ions such as fluoride, chloride, magnesium sodium, potassium, etc.), or combinations or derivatives thereof.

In some embodiments, tissue will infiltrate the matrix to a degree of about at least 50 percent within about 1 month to about 6 months after implantation of the matrix. In some embodiments, about 75 percent of the matrix will be infiltrated by tissue within about 2-3 months after implantation of the matrix. In some embodiments, the matrix will be substantially, e.g., about 90 percent or more, submerged in or enveloped by tissue within about 6 months after implantation of the matrix. In some embodiments, the matrix will be completely submerged in or enveloped by tissue within about 9-12 months after implantation.

In some embodiments, the matrix has a thickness of from 0.25 mm to 5 mm, or from about 0.4 mm to about 2 mm, or 0.4 mm to about 1 mm. Clearly, different bone defects (e.g., osteochondral defects) may require different matrix thicknesses.

In some embodiments, the matrix has a density of between about 1.6 $g/cm^3$, and about 0.05 $g/cm^3$. In some embodiments, the matrix has a density of between about 1.1 $g/cm^3$, and about 0.07 $g/cm^3$. For example, the density may be less than about 1 $g/cm^3$, less than about 0.7 $g/cm^3$, less than about 0.6 $g/cm^3$, less than about 0.5 $g/cm^3$, less than about 0.4 $g/cm^3$, less than about 0.3 $g/cm^3$, less than about 0.2 $g/cm^3$, or less than about 0.1 $g/cm^3$.

The shape of the matrix may be tailored to the site at which it is to be situated. For example, it may be in the shape of a morsel, a plug, a pin, a peg, a cylinder, a block, a wedge, a sheet, etc.

In some embodiments, the diameter or diagonal of the matrix can range from 1 mm to 50 mm. In some embodiments, the diameter or diagonal of the matrix can range from 1 mm to 30 mm, or 5 mm to 10 mm which is small enough to fit through an endoscopic cannula, but large enough to minimize the number of matrices needed to fill a large the bone defect (e.g., osteochondral defect).

In some embodiments, the matrix may be made by injection molding, compression molding, blow molding, thermoforming, die pressing, slip casting, electrochemical machining, laser cutting, water-jet machining, electrophoretic deposition, powder injection molding, sand casting, shell mold casting, lost tissue scaffold casting, plaster-mold casting, ceramic-mold casting, investment casting, vacuum casting, permanent-mold casting, slush casting, pressure casting, die casting, centrifugal casting, squeeze casting, rolling, forging, swaging, extrusion, shearing, spinning, powder metallurgy compaction or combinations thereof In some embodiments, a therapeutic agent (including one or more growth factors) may be disposed on or in the matrix by hand, electrospraying, ionization spraying or impregnating, vibratory dispersion (including sonication), nozzle spraying, compressed-air-assisted spraying, brushing and/or pouring. For example, a growth factor such as rhBMP-2 may be disposed on or in the matrix.

In some embodiments, the matrix may comprise sterile and/or preservative free material.

The matrix can be implanted by hand or machine in procedures such as for example, laparoscopic, arthroscopic, neuroendoscopic, endoscopic, rectoscopic procedures or the like.

Growth Factors

In some embodiments, a growth factor and/or therapeutic agent may be disposed on or in the matrix by hand, electrospraying, ionization spraying or impregnating, vibratory dispersion (including sonication), nozzle spraying, compressed-air-assisted spraying, brushing and/or pouring. For example, a growth factor such as rhBMP-2 may be disposed on or in the biodegradable carrier by the surgeon before the biodegradable matrix is administered or it may be available from the manufacturer beforehand.

The biodegradable matrix may comprise at least one growth factor. These growth factors include osteoinductive agents (e.g., agents that cause new bone growth in an area where there was none) and/or osteoconductive agents (e.g., agents that cause ingrowth of cells into and/or through the matrix). Osteoinductive agents can be polypeptides or polynucleotides compositions. Polynucleotide compositions of the osteoinductive agents include, but are not limited to, isolated Bone Morphogenic Protein (BMP), Vascular Endothelial Growth Factor (VEGF), Connective Tissue Growth Factor (CTGF), Osteoprotegerin, Growth Differentiation Factors (GDFs), Cartilage Derived Morphogenic Proteins (CDMPs), Lim Mineralization Proteins (LMPs), Platelet derived growth factor, (PDGF or rhPDGF), Insulin-like growth factor (IGF) or Transforming Growth Factor beta (TGF-beta) polynucleotides. Polynucleotide compositions of the osteoinductive agents include, but are not limited to, gene therapy vectors harboring polynucleotides encoding the osteoinductive polypeptide of interest. Gene therapy methods often utilize a polynucleotide, which codes for the osteoinductive polypeptide operatively linked or associated to a promoter or any other genetic elements necessary for the expression of the osteoinductive polypeptide by the target tissue. Such gene therapy and delivery techniques are known in the art (see, for example, International Publication No. WO90/11092, the disclosure of which is herein incorporated by reference in its entirety). Suitable gene therapy vectors include, but are not limited to, gene therapy vectors that do not integrate into the host genome. Alternatively, suitable gene therapy vectors include, but are not limited to, gene therapy vectors that integrate into the host genome.

In some embodiments, the polynucleotide is delivered in plasmid formulations. Plasmid DNA or RNA formulations refer to polynucleotide sequences encoding osteoinductive polypeptides that are free from any delivery vehicle that acts to assist, promote or facilitate entry into the cell, including viral sequences, viral particles, liposome formulations, lipofectin, precipitating agents or the like. Optionally, gene therapy compositions can be delivered in liposome formulations and lipofectin formulations, which can be prepared by methods well known to those skilled in the art. General methods are described, for example, in U.S. Pat. Nos. 5,593,972, 5,589,466, and 5,580,859, the disclosures of which are herein incorporated by reference in their entireties.

Gene therapy vectors further comprise suitable adenoviral vectors including, but not limited to for example, those described in U.S. Pat. No. 5,652,224, which is herein incorporated by reference.

Polypeptide compositions of the isolated osteoinductive agents include, but are not limited to, isolated Bone Morphogenic Protein (BMP), Vascular Endothelial Growth Factor (VEGF), Connective Tissue Growth Factor (CTGF), Osteoprotegerin, Growth Differentiation Factors (GDFs), Cartilage Derived Morphogenic Proteins (CDMPs), Lim Mineralization Proteins (LMPs), Platelet derived growth factor, (PDGF or rhPDGF), Insulin-like growth factor (IGF) or Transforming Growth Factor beta (TGF-beta707) polypeptides. Polypeptide compositions of the osteoinductive agents include, but are not limited to, full length proteins, fragments or variants thereof.

Variants of the isolated osteoinductive agents include, but are not limited to, polypeptide variants that are designed to increase the duration of activity of the osteoinductive agent in vivo. Typically, variant osteoinductive agents include, but are not limited to, full length proteins or fragments thereof that are conjugated to polyethylene glycol (PEG) moieties to increase their half-life in vivo (also known as pegylation). Methods of pegylating polypeptides are well known in the art (See, e.g., U.S. Pat. No. 6,552,170 and European Pat. No. 0,401,384 as examples of methods of generating pegylated polypeptides). In some embodiments, the isolated osteoinductive agent(s) are provided as fusion proteins. In one embodiment, the osteoinductive agent(s) are available as fusion proteins with the Fc portion of human IgG. In another embodiment, the osteoinductive agent(s) are available as hetero- or homodimers or multimers. Examples of some fusion proteins include, but are not limited to, ligand fusions between mature osteoinductive polypeptides and the Fc portion of human Immunoglobulin G (IgG). Methods of making fusion proteins and constructs encoding the same are well known in the art.

Isolated osteoinductive agents that are included within a matrix are typically sterile. In a non-limiting method, sterility is readily accomplished for example by filtration through sterile filtration membranes (e.g., 0.2 micron membranes or filters). In one embodiment, the isolated osteoinductive agents include one or more members of the family of Bone Morphogenic Proteins ("BMPs"). BMPs are a class of proteins thought to have osteoinductive or growth-promoting activities on endogenous bone tissue, or function as procollagen precursors. Known members of the BMP family include, but are not limited to, BMP-1, BMP-2, BMP-3, BMP-4, BMP-5, BMP-6, BMP-7, BMP-8, BMP-9, BMP-10, BMP-11, BMP-12, BMP-13, BMP-15, BMP-16, BMP-17, BMP-18 as well as polynucleotides or polypeptides thereof, as well as mature polypeptides or polynucleotides encoding the same.

BMPs utilized as osteoinductive agents comprise one or more of BMP-1; BMP-2; BMP-3; BMP-4; BMP-5; BMP-6; BMP-7; BMP-8; BMP-9; BMP-10; BMP-11; BMP-12; BMP-13; BMP-15; BMP-16; BMP-17; or BMP-18; as well as any combination of one or more of these BMPs, including full length BMPs or fragments thereof, or combinations thereof, either as polypeptides or polynucleotides encoding the polypeptide fragments of all of the recited BMPs. The isolated BMP osteoinductive agents may be administered as polynucleotides, polypeptides, full length protein or combinations thereof.

In another embodiment, isolated osteoinductive agents include osteoclastogenesis inhibitors to inhibit bone resorption of the bone tissue surrounding the site of implantation by osteoclasts. Osteoclast and osteoclastogenesis inhibitors include, but are not limited to, osteoprotegerin polynucleotides or polypeptides, as well as mature osteoprotegerin proteins, polypeptides or polynucleotides encoding the same. Osteoprotegerin is a member of the TNF-receptor superfamily and is an osteoblast-secreted decoy receptor that functions as a negative regulator of bone resorption. This protein specifically binds to its ligand, osteoprotegerin ligand (TNFSF11/OPGL), both of which are key extracellular regulators of osteoclast development.

Osteoclastogenesis inhibitors further include, but are not limited to, chemical compounds such as bisphosphonate, 5-lipoxygenase inhibitors such as those described in U.S. Pat. Nos. 5,534,524 and 6,455,541 (the contents of which are herein incorporated by reference in their entireties), heterocyclic compounds such as those described in U.S. Pat. No. 5,658,935 (herein incorporated by reference in its entirety), 2,4-dioxoimidazolidine and imidazolidine derivative compounds such as those described in U.S. Pat. Nos. 5,397,796 and 5,554,594 (the contents of which are herein incorporated by reference in their entireties), sulfonamide derivatives such as those described in U.S. Pat. No. 6,313,119 (herein incorporated by reference in its entirety), or acylguanidine compounds such as those described in U.S. Pat. No. 6,492,356 (herein incorporated by reference in its entirety).

In another embodiment, isolated osteoinductive agents include one or more members of the family of Connective Tissue Growth Factors ("CTGFs"). CTGFs are a class of proteins thought to have growth-promoting activities on connective tissues. Known members of the CTGF family include, but are not limited to, CTGF-1, CTGF-2, CTGF-4 polynucleotides or polypeptides thereof, as well as mature proteins, polypeptides or polynucleotides encoding the same.

In another embodiment, isolated osteoinductive agents include one or more members of the family of Vascular Endothelial Growth Factors ("VEGFs"). VEGFs are a class of proteins thought to have growth-promoting activities on vascular tissues. Known members of the VEGF family include, but are not limited to, VEGF-A, VEGF-B, VEGF-C, VEGF-D, VEGF-E or polynucleotides or polypeptides thereof, as well as mature VEGF-A, proteins, polypeptides or polynucleotides encoding the same.

In another embodiment, isolated osteoinductive agents include one or more members of the family of Transforming Growth Factor-beta ("TGFbetas"). TGF-betas are a class of proteins thought to have growth-promoting activities on a range of tissues, including connective tissues. Known members of the TGF-beta family include, but are not limited to, TGF-beta-1, TGF-beta-2, TGF-beta-3, polynucleotides or polypeptides thereof, as well as mature protein, polypeptides or polynucleotides encoding the same.

In another embodiment, isolated osteoinductive agents include one or more Growth Differentiation Factors ("GDFs"). Known GDFs include, but are not limited to, GDF-1, GDF-2, GDF-3, GDF-7, GDF-10, GDF-11, and GDF-15. For example, GDFs useful as isolated osteoinductive agents include, but are not limited to, the following GDFs: GDF-1 polynucleotides or polypeptides corresponding to GenBank Accession Numbers M62302, AAA58501, and AAB94786, as well as mature GDF-1 polypeptides or polynucleotides encoding the same. GDF-2 polynucleotides or polypeptides corresponding to GenBank Accession Numbers BC069643, BC074921, Q9UK05, AAH69643, or AAH74921, as well as mature GDF-2 polypeptides or polynucleotides encoding the same. GDF-3 polynucleotides or polypeptides corresponding to GenBank Accession Numbers AF263538, BCO30959, AAF91389, AAQ89234, or Q9NR23, as well as mature GDF-3 polypeptides or polynucleotides encoding the same. GDF-7 polynucleotides or polypeptides corresponding to GenBank Accession Numbers AB158468, AF522369, AAP97720, or Q7Z4P5, as well as mature GDF-7 polypeptides or polynucleotides encoding the same. GDF-10 polynucleotides or polypeptides corresponding to GenBank Accession Numbers BC028237 or AAH28237, as well as mature GDF-10 polypeptides or polynucleotides encoding the same.

GDF-11 polynucleotides or polypeptides corresponding to GenBank Accession Numbers AF100907, NP_005802 or 095390, as well as mature GDF-11 polypeptides or polynucleotides encoding the same. GDF-15 polynucleotides or polypeptides corresponding to GenBank Accession Numbers BC008962, BC000529, AAH00529, or NP_004855, as well as mature GDF-15 polypeptides or polynucleotides encoding the same.

In another embodiment, isolated osteoinductive agents include Cartilage Derived Morphogenic Protein (CDMP) and Lim Mineralization Protein (LMP) polynucleotides or polypeptides. Known CDMPs and LMPs include, but are not limited to, CDMP-1, CDMP-2, LMP-1, LMP-2, or LMP-3.

CDMPs and LMPs useful as isolated osteoinductive agents include, but are not limited to, the following CDMPs and LMPs: CDMP-1 polynucleotides and polypeptides corresponding to GenBank Accession Numbers NM_000557, U13660, NP_000548 or P43026, as well as mature CDMP-1 polypeptides or polynucleotides encoding the same. CDMP-2 polypeptides corresponding to GenBank Accession Numbers or P55106, as well as mature CDMP-2 polypeptides. LMP-1 polynucleotides or polypeptides corresponding to GenBank Accession Numbers AF345904 or AAK30567, as well as mature LMP-1 polypeptides or polynucleotides encoding the same. LMP-2 polynucleotides or polypeptides corresponding to GenBank Accession Numbers AF345905 or AAK30568, as well as mature LMP-2 polypeptides or polynucleotides encoding the same. LMP-3 polynucleotides or polypeptides corresponding to GenBank Accession Numbers AF345906 or AAK30569, as well as mature LMP-3 polypeptides or polynucleotides encoding the same.

In another embodiment, isolated osteoinductive agents include one or more members of any one of the families of Bone Morphogenic Proteins (BMPs), Connective Tissue Growth Factors (CTGFs), Vascular Endothelial Growth Factors (VEGFs), Osteoprotegerin or any of the other osteoclastogenesis inhibitors, Growth Differentiation Factors (GDFs), Cartilage Derived Morphogenic Proteins (CDMPs), Lim Mineralization Proteins (LMPs), or Transforming Growth Factor-betas (TGF-betas), as well as mixtures or combinations thereof.

In another embodiment, the one or more isolated osteoinductive agents useful in the bioactive formulation are selected from the group consisting of BMP-1, BMP-2, BMP-3, BMP- 4, BMP-5, BMP-6, BMP-7, BMP-8, BMP-9, BMP-10, BMP-11, BMP-12, BMP-13, BMP-15, BMP-16, BMP-17, BMP-18, or any combination thereof; CTGF-1, CTGF-2, CGTF-3, CTGF-4, or any combination thereof; VEGF-A, VEGF-B, VEGF-C, VEGF-D, VEGF-E, or any combination thereof; GDF-1, GDF-2, GDF-3, GDF-7, GDF-10, GDF-11, GDF-15, or any combination thereof; CDMP-1, CDMP-2, LMP-1, LMP-2, LMP-3, and/or any combination thereof; Osteoprotegerin; TGF-beta-1, TGF-beta-2, TGF-beta-3, or any combination thereof; or any combination of one or more members of these groups.

In some embodiments, BMP-7 and/or GDF-5 may be used at 1-2 mg/cc of matrix.

The concentrations of growth factor can be varied based on the desired length or degree of osteogenic effects desired. Similarly, one of skill in the art will understand that the duration of sustained release of the growth factor can be modified by the manipulation of the compositions comprising the sustained release formulation, such as for example, modifying the percent of polymers found within a sustained release formulation, microencapsulation of the formulation within polymers, including polymers having varying degradation times and characteristics, and layering the formulation in varying thicknesses in one or more degradable polymers. These sustained release formulations can therefore be designed to provide customized time release of growth factors that stimulate the natural healing process.

The growth factor may contain inactive materials such as buffering agents and pH adjusting agents such as potassium bicarbonate, potassium carbonate, potassium hydroxide, sodium acetate, sodium borate, sodium bicarbonate, sodium carbonate, sodium hydroxide or sodium phosphate; degradation/release modifiers; drug release adjusting agents; emulsifiers; preservatives such as benzalkonium chloride, chlorobutanol, phenylmercuric acetate and phenylmercuric nitrate, sodium bisulfate, sodium bisulfite, sodium thiosulfate, thimerosal, methylparaben, polyvinyl alcohol and phenylethyl alcohol; solubility adjusting agents; stabilizers; and/or cohesion modifiers. In some embodiments, the growth factor may comprise sterile and/or preservative free material.

These above inactive ingredients may have multi-functional purposes including the carrying, stabilizing and controlling the release of the growth factor and/or other therapeutic agent(s). The sustained release process, for example, may be by a solution-diffusion mechanism or it may be governed by an erosion-sustained process.

In some embodiments, a pharmaceutically acceptable formulation comprising a growth factor is provided, wherein the formulation is a freeze-dried or lyophilized formulation. Typically, in the freeze-dried or lyophilized formulation an effective amount of a growth factor is provided. Lyophilized formulations can be reconstituted into solutions, suspensions, emulsions, or any other suitable form for administration or use. The lyophilized formulation may comprise the coloring agent or the liquid used to reconstitute the growth factor may contain the coloring agent. Lyophilized formulations are typically first prepared as liquids, then frozen and lyophilized. The total liquid volume before lyophilization can be less, equal to, or more than, the final reconstituted volume of the lyophilized formulation. The lyophilization process is well known to those of ordinary skill in the art, and typically includes sublimation of water from a frozen formulation under controlled conditions.

Lyophilized formulations can be stored at a wide range of temperatures. Lyophilized formulations may be stored at or below 30° C., for example, refrigerated at 4° C., or at room temperature (e.g., approximately 25° C.).

Lyophilized formulations of the growth factor are typically reconstituted for use by addition of an aqueous solution to dissolve the lyophilized formulation. A wide variety of aqueous solutions can be used to reconstitute a lyophilized formulation. In some embodiments, lyophilized formulations are reconstituted using water. In some embodiments, the coloring agent may be added to the diluent that reconstitutes the growth factor. In some embodiments, lyophilized formulations can be reconstituted with a solution containing water (e.g., USP WFI, or water for injection) or bacteriostatic water (e.g., USP WFI with 0.9% benzyl alcohol). However, solutions comprising buffers and/or excipients and/or one or more pharmaceutically acceptable carries can also be used. In some embodiments, the solutions do not contain any preservatives (e.g., are preservative free).

In some embodiments, the lyophilized growth factor (e.g., BMP) can be disposed in a vial by the manufacturer and then the surgeon can mix the diluent containing the coloring agent with the lyophilized growth factor. This mixture can then be parenterally administered to the target tissue site. The term "parenteral" as used herein refers to modes of administration which bypass the gastrointestinal tract, and include for example, intramuscular, intraperitoneal, intrasternal, subcutaneous, intra-operatively, intrathecally, intradiskally, peridiskally, epidurally, perispinally, intraarticular or combinations thereof.

In some embodiments, the growth factor (e.g., BMP) is a colorless solution and the coloring agent can be added to the colorless solution so that the user can now see the growth factor's application to the target tissue site and/or matrix. In some embodiments, the mixture of growth factor and coloring agent is applied to the matrix and then the user can view its distribution on the matrix.

The amount of growth factor, e.g., bone morphogenic protein may be sufficient to cause bone and/or cartilage growth. In some embodiments, the growth factor is rhBMP-2 and is contained in one or more matrices in an amount of from 1 to 2 mg per cubic centimeter of the biodegradable matrix. In some embodiments, the amount of rhBMP-2 morphogenic protein is from 2.0 to 2.5 mg per cubic centimeter (cc) of the biodegradable matrix.

In some embodiments, the growth factor is supplied in a liquid carrier (e.g., an aqueous buffered solution). Exemplary aqueous buffered solutions include, but are not limited to, TE, HEPES (2-[4-(2-hydroxyethyl)-1-piperazinyl]ethanesulfonic acid), MES (2-morpholinoethanesulfonic acid), sodium acetate buffer, sodium citrate buffer, sodium phosphate buffer, a Tris buffer (e.g., Tris-HCL), phosphate buffered saline (PBS), sodium phosphate, potassium phosphate, sodium chloride, potassium chloride, glycerol, calcium chloride or a combination thereof. In various embodiments, the buffer concentration can be from about 1 mM to 100 mM. In some embodiments, the BMP-2 is provided in a vehicle (including a buffer) containing sucrose, glycine, L-glutamic acid, sodium chloride, and/or polysorbate 80.

In some embodiments, upon implantation of the matrix or components that contact the matrix (e.g., plugs that are separate from the matrix on implantation), some compression of the matrix occurs that causes the buffer from the bone growth factor to leak from the carrier, which causes higher concentrations of the growth factor (e.g., 2 mg to 2.5 mg of rhBMP-2 per cc of matrix) to remain on the matrix. This high concentration of growth factor may lead to local transient bone resorption and excess osteoclast formation and bone breakdown. This may result in poor integration of the plug graft with surrounding host tissue and a failed repair. In some embodiments, localized release of the growth factor may cause local irritation to the surrounding tissue. In some embodiments, the leaking of growth factor from the matrix may reduce a stable microenvironment for new bone and/or cartilage growth. It also may cause the matrix to fail to retain its full efficacy over time to maximally promote bone growth at a target site.

In some embodiments, some compression may cause the growth factor from the upper part of the matrix to migrate to the lower part and thus cause a low concentration of growth factor (e.g., 0.05 mg to 1 mg of rhBMP-2 per cc of matrix) on the upper part of the matrix to be exposed to the microenvironment of the defect, which may promote cartilage formation at the site the matrix is implanted. In some instances, this may be desirable especially where more cartilage tissue is needed.

In some embodiments, when the matrix is used in conjunction with osteochondral plugs, if compression occurs, the pores of the matrix get closed and the plug drops from the surface of the cartilage so the surface of the plug is no longer flush with the surface of the cartilage. This will cause poor tissue growth.

In some embodiments, a method is provided for accelerating bone repair in a patient in need of such treatment, the method comprising mixing a growth factor (e.g., bone morphogenic protein-2) and a coloring agent to form a mixture, wherein the coloring agent imparts color to the mixture; applying the mixture to a surface of a porous collagen matrix, wherein the coloring agent allows the user to see the growth factor distribution on or in the porous collagen matrix; and implanting the porous collagen matrix at or near a target tissue site in need of bone repair. In this way, the user can see the distribution of the growth factor on the matrix and/or see the matrix is over-compressed by the leakage of the coloring agent from the matrix.

Coloring Agent

By adding a coloring agent to growth factor, the user can visualize if excessive compression of the matrix occurs by looking for growth factor leakage simply by watching for the color. In this way, if a color is visualized off the matrix, the user can discard the matrix, remove the leakage with a suctioning instrument or, if compression is not excessive, stop pressing on the matrix.

In some embodiments, by adding a coloring agent to the growth factor, the user can visualize not only compression of the matrix, but also application of the coloring agent to the matrix. The user can view the matrix and determine if the growth factor has been applied to one or more surfaces of the matrix or if the growth factor is uniformly distributed on or in the matrix simply by viewing the color distribution along the matrix.

In some embodiments, to ease viewing, the coloring agent may have a color in stark contrast to the matrix. For example, the matrix may be white or beige and the coloring agent with growth factor may be green or blue. In this way, the growth factor can easily be seen. In some embodiments, the coloring agent and/or matrix may be a color that is in stark contrast to surrounding tissue and/or blood. For example, the color red may be avoided if the procedure will be bloody.

It will be understood by those of ordinary skill in the art that some compression may occur to release the growth factor (e.g., less than 0.75 M Pa, or 0.5 M Pa, or 0.25 M Pa of pressure), which may release less than 10%, 9%, 8%, 7%, 6%, 5%, 4%, 3%, 2%, 1%, or 0.5% w/w or w/v of the growth factor. The matrix may be in a compressed state, for example, when more than 20%, 30%, 40%, 50%, 60%, 70%, 80%, 90%, 99%, or all of the growth factor leaks out of the matrix.

Coloring agents that may be used to color the growth factor include commercially available natural and artificial colorants. One or more coloring agents are included in growth factor formulation or they can be added to it at the time of use or by the manufacturer and then reconstituted at the time of use.

The coloring agent can be in the osteogenic composition in an amount of between about 0.5% and 99%, or between 1% and 90%, or between 10% and 70% or between 20% and 50%, or between about 1% and about 20%, or between about 0.5% and about 10% (w/w, w/v, or v/v) with respect to the total composition (w/w, w/v, v/v) to impart the desired color to the growth factor.

In some embodiments, the coloring agent will be separate from the buffer and the growth factor. In some embodiments, the coloring agent and the liquid buffer (e.g., containing sucrose, glycine, L-glutamic acid, sodium chloride, and/or polysorbate 80) will be together in one vial, which can be used to reconstitute lyophilized or freeze dried growth factor (e.g., rhBMP-2), which is also in a separate vial. Once the two are mixed, the user can now visualize administration of the growth factor.

Color is understood to mean any color in the visible spectrum. In some embodiments, the specific color of the coloring agent is transmitted in visible light. In some embodiments, the color of the coloring agent can be red, yellow, green, blue, violet, or the like. The coloring agent is understood to mean a material intended to give a color to a material or composition. The coloring agent may comprise a pigment for it to give the desired color. Pigments are natural or synthetic substances composed of fine particles which, in contrast to dyes, are often insoluble in their medium of use, the main function of which is to give a coloring. Pigments may be inorganic pigments, organic pigments (e.g., carbon black (Cl 77 266) or D & C Red 36), lakes or pearlescent pigments. Lakes are dyes adsorbed on insoluble particles, the combination remaining essentially insoluble in the medium of use. Pearlescent pigments are natural or synthetic substances which scatter and reflect light to give an iridescent or bright effect. The dyes may include natural organic dyes, such as cochineal carmine (Cl 75 470), or synthetic organic dyes, such as haloacid, azo or anthraquinone dyes. Dyes may include inorganic dyes, such as copper sulphate.

Inorganic pigments of metal oxides in particular zirconium, cerium, zinc or chromium oxides (Cl 77 288), titanium dioxide (Cl 77 891), black, yellow, red and brown iron oxides (Cl 77 499, Cl 77 492 or Cl 77 491), manganese violet (Cl 77 742), ultramarine blue (Cl 77 007), iron blue (Cl 77 510), chromium hydrate (Cl 77 289), silver powder or aluminium powder or combinations thereof may be used.

Lakes are generally composed of metal salts (in particular Al, Zr, Ca or Na) of organic dyes adsorbed on particles, for example of alumina, of barium sulphate, of colophony, and the like. Lakes include those known under the names: D & C Red 21 (Cl 45 380), D & C Orange 5 (Cl 45 370), D & C Red 27 (Cl 45 410), D & C Orange 10 (Cl 45 425), D & C Red 3 (Cl 45 430), D & C Red 7 (Cl 15 850:1), D & C Red 4 (Cl 15 510), D & C Red 33 (Cl 17 200), D & C Yellow 5 (Cl 19 140), D & C Yellow 6 (Cl 15 985), D & C Green 5 (Cl 61 570), D & C Yellow 10 (Cl 77 002), D & C Green 3 (Cl 42 053), D & C Blue 1 (Cl 42 090).

Pearlescent pigments may include bismuth oxychloride or mica covered with titanium oxide, with iron oxide or with natural pigments, for example colored titanium dioxide-coated mica. A combination of one or more above coloring agents can be used to produce the desired color of the formulation.

In some embodiments, the coloring agent maintains its color before, during and after mixing. For example, in some embodiments, the coloring agent does not need certain pH and/or temperature characteristics to occur to promote a change of color (e.g., pH causing red to blue color change, or temperature to cause clear to blue color). Rather, in some embodiments, the coloring agent maintains its color before, during and after mixing with the growth factor and/or diluent. Thus, in this embodiment, no special UV light, or detection instrument is needed and the coloring agent will maintain its color during the period of mixing and administering the growth factor. The coloring agent will be visibly apparent to the naked eye of a person of normal color vision. This is unlike thermosetting dyes or pH sensitive dyes that change color when certain pH or temperature is reached.

In some embodiments, the coloring agent (thus the growth factor when mixed) will be readily visible to the human eye (including a user wearing glasses, face shield and/or contacts). Some exemplary coloring agents are synthetic or natural agents that are FDA approved. These include D&C violet #2, D&C red #22, D&C red #27, D&C red #28, D&C red #33, D&C orange #4, D&C yellow #10, D&C green #5, D&C green #8, D&C red No. 6 barium lake, D&C Red No. 7 calcium lake, D&C red No. 7 calcium lake, D&C red No. 7 calcium lake, D&C red No. 27 aluminum lake, D&C red No. 27 Zr/Al titanium 02 lake, D&C red No. 28 aluminum lake, D&C red No. 30 talc lake, D&C yellow No. 10 aluminum lake, FD&C blue 1, FD&C green 3, FD&C red 40, FD&C yellow 5, FD&C yellow 6, D&C green 5, D&C green 8, D&C orange 4. D&C orange 5, D&C red 22, D&C red 33D, D&C violet 2, annatto, bismuth oxychloride, carmine carotene-beta, chromium hydroxide green, chromium oxide greens, ferric ferrocyanide, henna, iron oxides, manganese violet, mica, titanium dioxide, ultramarines, zinc oxide or a combination thereof.

In some embodiments, the colorant comprises one or more of FD&C blue No. 1—brilliant blue FCF, E133 (blue shade), FD&C blue No. 2—indigotine, E132 (dark blue shade), FD&C green No. 3—fast green FCF, E143 (bluish green shade), FD&C red No. 40—allura red AC, E129 (red shade), FD&C red No. 3—erythrosine, E127 (pink shade), FD&C yellow No. 5—tartrazine, E102 (yellow shade), FD&C yellow No. 6—sunset yellow FCF, E110 (orange shade), congo red, indigo, methylene blue, or a combination thereof.

In some embodiments, the coloring agent is approved by the U.S. FDA for use in or on medical devices. These coloring agents include chromium oxide greens (blue-green pigment), phthalocyanine green (pigment), 7,16-Dichloro-6,15-dihydro-5,9,14,18-anthrazinetetrone or C.I. Vat blue 6 (Vat Dye), 7,16-Dichloro-6,15-dihydro-5,9,14,18-anthrazinetetrone or C.I. Vat Green (vat Dye), D&C Blue No. 9 (A.C.I., Vat Blue 6 with other additives), FD&C Blue No. 2 (Lake), D&C Blue No. 6 (water soluble dye), D&C Green No. 5 (pigment), D&C Green No. 6 (water soluble dye), or a combination thereof.

In some embodiments, the coloring agent may be visible by instrument, such as for example, magnifying glass, microscope, spectrophotometer at a given wavelength.

Typically, the growth factor and coloring agent may be provided to the physician as two-phase or three-phase system that comprises a liquid diluent (e.g., WFI and the coloring agent) and growth factor or the diluent, coloring agent and the growth factor separately or the growth factor and/or coloring agent may be disposed on or in the matrix and the diluent can be applied to the matrix to reconstitute the growth factor and/or coloring agent. The user will be able to see the application of the growth factor. The growth factor, and/or coloring agent may be in different forms (e.g., powder, liquid, gel form, etc.). These can be mixed in the operating room in a vacuum-mixing chamber (or alternatively, may be mixed without using a vacuum-mixing chamber), distributed on or in the matrix and inserted into the prepared bone cavity.

In some embodiments, the coloring agent does not interfere or substantially interfere with the growth factor and/or matrix function.

Additional Therapeutic Agents

The growth factors of the present application may be disposed on or in the matrix with other therapeutic agents. For example, the growth factor may be disposed on or in the carrier by electrospraying, ionization spraying or impregnating, vibratory dispersion (including sonication), nozzle spraying, compressed-air-assisted spraying, brushing and/or pouring.

Exemplary therapeutic agents include but are not limited to IL-1 inhibitors, such Kineret® (anakinra), which is a recombinant, non-glycosylated form of the human interleukin-1 receptor antagonist (IL-1Ra), or AMG 108, which is a monoclonal antibody that blocks the action of IL-1. Therapeutic agents also include excitatory amino acids such as glutamate and aspartate, antagonists or inhibitors of glutamate binding to NMDA receptors, AMPA receptors, and/or kainate receptors. Interleukin-1 receptor antagonists, thalidomide (a TNF-α release inhibitor), thalidomide analogues (which reduce TNF-α production by macrophages), quinapril (an inhibitor of angiotensin II, which upregulates TNF-α), interferons such as IL-11 (which modulate TNF-α receptor expression), and aurin-tricarboxylic acid (which inhibits TNF-α), may also be useful as therapeutic agents for reducing inflammation. It is further contemplated that where desirable a pegylated form of the above may be used. Examples of still other therapeutic agents include NF kappa B inhibitors such as antioxidants, such as dilhiocarbamate, and other compounds, such as, for example, sulfasalazine.

Examples of therapeutic agents suitable for use also include, but are not limited to, an anti-inflammatory agent, analgesic agent, or osteoinductive growth factor or a combination thereof. Anti-inflammatory agents include, but are not limited to, apazone, celecoxib, diclofenac, diflunisal, enolic acids (piroxicam, meloxicam), etodolac, fenamates (mefenamic acid, meclofenamic acid), gold, ibuprofen, indomethacin, ketoprofen, ketorolac, nabumetone, naproxen, nimesulide, salicylates, sulfasalazine[2-hydroxy-5-[4-[C2-pyridinylamino)sulfonyl]azo]benzoic acid, sulindac, tepoxalin, and tolmetin; as well as antioxidants, such as dithiocarbamate, steroids, such as cortisol, cortisone, hydrocortisone, fludrocortisone, prednisone, prednisolone, methylprednisolone, triamcinolone, betamethasone, dexamethasone, beclomethasone, fluticasone or a combination thereof.

Suitable analgesic agents include, but are not limited to, acetaminophen, bupivicaine, fluocinolone, lidocaine, opioid analgesics such as buprenorphine, butorphanol, dextromoramide, dezocine, dextropropoxyphene, diamorphine, fentanyl, alfentanil, sufentanil, hydrocodone, hydromorphone, ketobemidone, levomethadyl, mepiridine, methadone, morphine, nalbuphine, opium, oxycodone, papaveretum, pentazocine, pethidine, phenoperidine, piritramide, dextropropoxyphene, remifentanil, tilidine, tramadol, codeine, dihydrocodeine, meptazinol, dezocine, eptazocine, flupirtine, amitriptyline, carbamazepine, gabapentin, pregabalin, or a combination thereof.

In some embodiments, a statin may be used. Statins include, but is not limited to, atorvastatin, simvastatin, pravastatin, cerivastatin, mevastatin (see U.S. Pat. No. 3,883,140, the entire disclosure is herein incorporated by reference), velostatin (also called synvinolin; see U.S. Pat. Nos. 4,448, 784 and 4,450,171 these entire disclosures are herein incorporated by reference), fluvastatin, lovastatin, rosuvastatin and fluindostatin (Sandoz XU-62-320), dalvastain (EP Appln. Publn. No. 738510 A2, the entire disclosure is herein incorporated by reference), eptastatin, pitavastatin, or pharmaceutically acceptable salts thereof or a combination thereof. In various embodiments, the statin may comprise mixtures of (+)R and (−)-S enantiomers of the statin. In various embodiments, the statin may comprise a 1:1 racemic mixture of the statin.

Kits

The matrix, coloring agent, growth factor and devices to administer the osteogenic composition may be sterilizable. In various embodiments, one or more components of the osteogenic composition, and/or medical device to administer it may be sterilizable by radiation in a terminal sterilization step in the final packaging. Terminal sterilization of a product provides greater assurance of sterility than from processes such as an aseptic process, which require individual product components to be sterilized separately and the final package assembled in a sterile environment.

Typically, in various embodiments, gamma radiation is used in the terminal sterilization step, which involves utilizing ionizing energy from gamma rays that penetrates deeply in the device. Gamma rays are highly effective in killing microorganisms, they leave no residues nor have sufficient energy to impart radioactivity to the device. Gamma rays can be employed when the device is in the package and gamma sterilization does not require high pressures or vacuum conditions, thus, package seals and other components are not stressed. In addition, gamma radiation eliminates the need for permeable packaging materials.

In some embodiments, the osteogenic composition may be packaged in a moisture resistant package and then terminally sterilized by gamma irradiation. In use the surgeon removes the one or all components from the sterile package for use.

In various embodiments, electron beam (e-beam) radiation may be used to sterilize one or more components of the device. E-beam radiation comprises a form of ionizing energy, which is generally characterized by low penetration and high-dose rates. E-beam irradiation is similar to gamma processing in that it alters various chemical and molecular bonds on contact, including the reproductive cells of microorganisms. Beams produced for e-beam sterilization are concentrated, highly-charged streams of electrons generated by the acceleration and conversion of electricity.

Other methods may also be used to sterilize the osteogenic composition and/or one or more components of the device, including, but not limited to, gas sterilization, such as, for example, with ethylene oxide or steam sterilization.

In various embodiments, a kit is provided comprising the growth factor, coloring agent, matrix, and/or diluents. The kit may include additional parts along with the osteogenic composition combined together to be used to implant the matrix (e.g., sponges, meshes etc.). The kit may include the matrix in a first compartment. The second compartment may include a vial holding the growth factor, diluent and coloring agent and any other instruments needed for the localized drug delivery. A third compartment may include gloves, drapes, wound dressings and other procedural supplies for maintaining sterility of the implanting process, as well as an instruction booklet, which may include a color chart that shows the color of the growth factor after reconstitution with the coloring agent. A fourth compartment may include additional needles and/or sutures. Each tool may be separately packaged in a plastic pouch that is radiation sterilized. A fifth compartment may include an agent for radiographic imaging. A cover of the kit may include illustrations of the implanting procedure and a clear plastic cover may be placed over the compartments to maintain sterility.

It will be apparent to those skilled in the art that various modifications and variations can be made to various embodiments described herein without departing from the spirit or scope of the teachings herein. Thus, it is intended that various embodiments cover other modifications and variations of various embodiments within the scope of the present teachings.

What is claimed is:

1. A method for accelerating bone repair in a patient in need of such treatment, the method comprising mixing an osteogenic composition comprising a growth factor and a coloring agent to form a mixture, wherein the coloring agent imparts color to the mixture; applying the mixture to a surface of a biodegradable matrix, wherein the coloring agent allows a user to see the growth factor on or in the matrix; and implanting the matrix at or near a target tissue site in need of bone repair, wherein the matrix comprises a density between 0.05 g/cm$^3$ to about 1.6 g/cm$^3$, a diagonal of 1 mm to 50 mm, and pores having a size of between about 10 micrometers to about 500 micrometers.

2. A method for accelerating bone repair according to claim 1, wherein the growth factor comprises a colorless solution and the coloring agent comprises a dye.

3. A method for accelerating bone repair according to claim 1, wherein the biodegradable matrix releases the growth factor and the coloring agent when the matrix is compressed for the user to see.

4. A method for accelerating bone repair according to claim 1, wherein the coloring agent comprises a color contrasting the color of the matrix.

5. A method for accelerating bone repair according to claim 1, wherein the color of the composition is visible to the naked eye.

6. A method for accelerating bone repair according to claim 1, wherein the coloring agent comprises a color contrasting the target tissue site.

7. A method for accelerating bone repair according to claim 1, wherein (i) the growth factor comprises bone morphogenic protein-2; (ii) the coloring agent comprises a dye; and (iii) the biodegradable matrix comprises porous collagen.

8. A method for accelerating bone repair according to claim 1, wherein the biodegradable matrix holds the growth factor and coloring agent when the matrix is in an uncompressed state.

9. A method for accelerating bone repair according to claim 1, wherein the biodegradable matrix comprises at least one of collagen, a resorbable polymer, gelatin, a resorbable ceramic or combinations thereof.

* * * * *

UNITED STATES PATENT AND TRADEMARK OFFICE
CERTIFICATE OF CORRECTION

| | | |
|---|---|---|
| PATENT NO. | : 8,188,038 B2 | |
| APPLICATION NO. | : 13/195343 | |
| DATED | : May 29, 2012 | |
| INVENTOR(S) | : McKay | |

It is certified that error appears in the above-identified patent and that said Letters Patent is hereby corrected as shown below:

In Column 9, Line 14, delete "thereof" and insert -- thereof. --, therefor.

In Column 12, Line 13, delete "BCO30959," and insert -- BC030959, --, therefor.

Signed and Sealed this
Twentieth Day of November, 2012

David J. Kappos
*Director of the United States Patent and Trademark Office*